US005652810A

United States Patent [19]
Tipton et al.

[11] Patent Number: 5,652,810
[45] Date of Patent: Jul. 29, 1997

[54] FIBER OPTIC SENSOR FOR SITE MONITORING

[75] Inventors: Terence L. Tipton, Panama City, Fla.; Brian S. Vogt, Greenville, S.C.

[73] Assignee: The United States of America as represented by the Secretary of the Air Force, Washington, D.C.

[21] Appl. No.: 647,214

[22] Filed: May 9, 1996

[51] Int. Cl.$^6$ ............................................. G02B 6/06
[52] U.S. Cl. .................. 385/12; 385/115; 385/13; 356/402; 250/227.15
[58] Field of Search .............. 385/12, 13, 115–121; 356/402; 250/227.14, 227.15; 128/667

[56] References Cited

U.S. PATENT DOCUMENTS 4,682,895  7/1987  Costello ................... 356/402

*Primary Examiner*—Phan T. H. Palmer
*Attorney, Agent, or Firm*—Bobby D. Scearce; Thomas L. Kundert

[57] ABSTRACT

A fiber optic sensor system for analyzing fluid systems is described which comprises a sampling probe which transmits tunable ultraviolet light to a sampling location, the probe including an optical fiber terminating in a sampling structure at the distal end of the probe which is inserted into the liquid to be analyzed, a light source for transmitting a selected excitation light beam to the sample location through the fiber, the resulting fluorescence characteristic of the liquid being transmitted back through the fiber structure to an optical detector. The sampling region at the end of the probe is configured to absorb or reflect away all excess excitation light so that only the resulting characteristic fluorescence is transmitted back to the detector, and may have a microporous base to exclude solid particles from the sampling region.

19 Claims, 1 Drawing Sheet

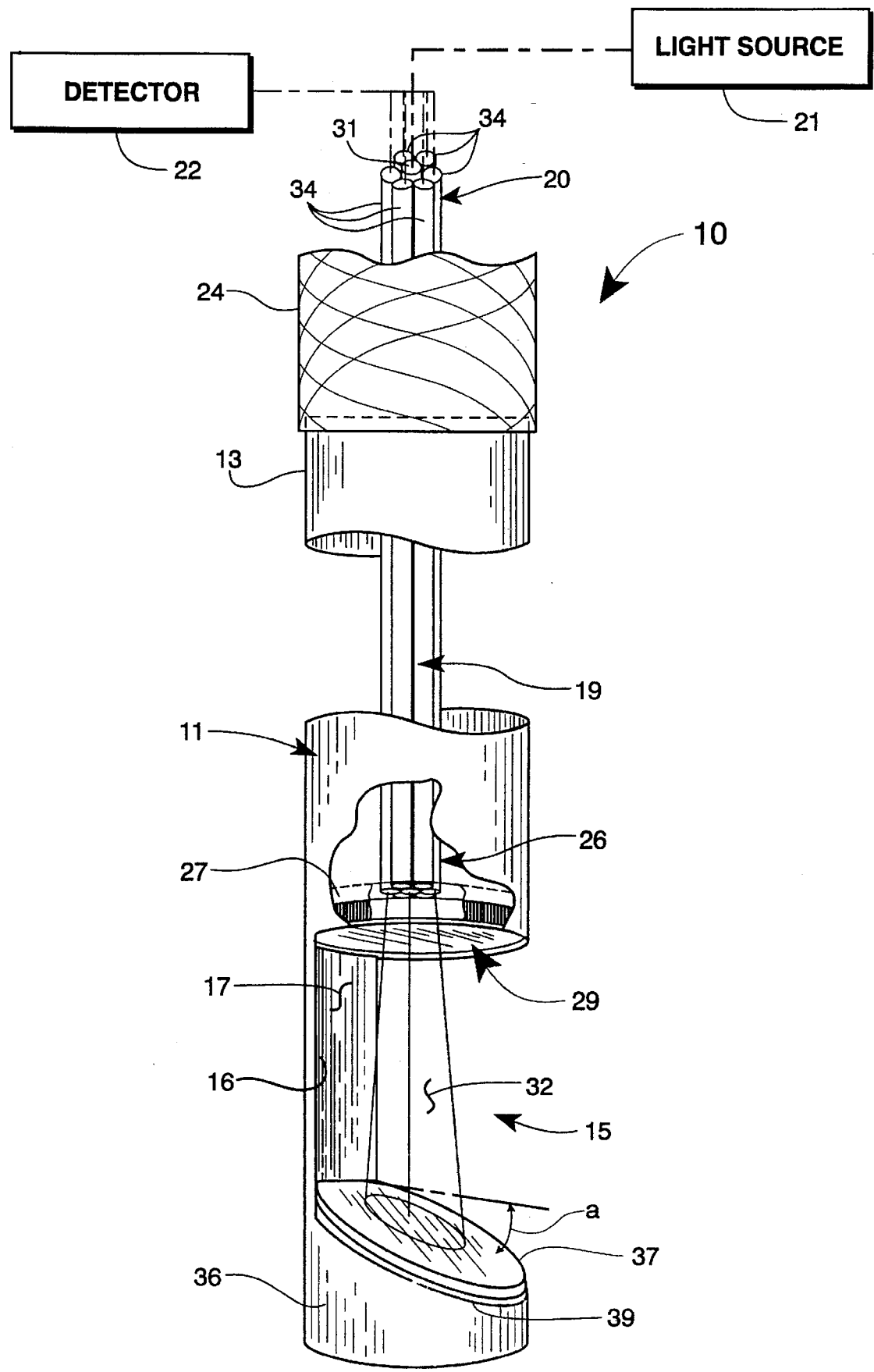

FIBER OPTIC SENSOR FOR SITE MONITORING

RIGHTS OF THE GOVERNMENT

The invention described herein may be manufactured and used by or for the Government of the United States for all governmental purposes without the payment of any royalty.

BACKGROUND OF THE INVENTION

The present invention relates generally to systems and methods for analysis of fluid systems using a probe, and more particularly to system and method for optically sampling and analysis of liquid systems using a fiber optic probe having particularly utility for in situ environmental monitoring.

Existing systems and methods for the measurement of pollutants in wells, aquifers and other environmental systems, are slow and cumbersome and substantially limited in their utility for in situ monitoring, and are limited in the ability to allow for turbidity, and other background interferences.

The invention solves or substantially reduces in critical importance problems with existing environmental monitoring systems by providing a fiber optic sensor probe which transmits tunable ultraviolet light to a remote monitoring location to permit quantitative measurements of an aqueous sample. The probe includes an optical fiber terminating in a sampling structure at the distal end of the probe which is inserted into the liquid to be analyzed, a selected excitation light beam is transmitted to the sample region through the fiber, and the resulting fluorescence characteristic of the liquid is transmitted back through the fiber structure to an optical detector. The sampling region at the end of the probe is configured to absorb or reflect away all excess excitation light so that only the resulting characteristic fluorescence is transmitted back to the detector, and may have a microporous base to exclude solid particles from the sampling region. The structure of the probe eliminates undesirable backscatter of light into the detector, has a fixed optical path length which allows turbidity corrections to be made, and is sufficiently compact to be used in model aquifer studies without significantly perturbing the aqueous flow. The invention may find particularly utility in the analysis of aromatic hydrocarbons via laser-induced fluorescence or Raman spectroscopy.

For the purpose of describing the invention and defining the scope thereof, the term "optical" shall, in accordance with customary usage, be defined herein to include only ultraviolet, visible, near infrared, mid-infrared and far infrared regions of the electromagnetic spectrum lying in the range of about 0.1 to about 1000 microns (see e.g., Garbuny, *Optical Physics*, Academic Press, NY (1965) pp 1–6), and more specifically the range from about 0.2 micron, the approximate lower limit of operation of fine quality quartz, to about 50 microns, the approximate upper limit of operation of long wavelength transmitting materials.

It is therefore a principal object of the invention to provide system and method for environmental monitoring.

It is another object of the invention to provide system and method for analysis of fluid systems using a probe.

It is another object of the invention to provide a portable system for on-site environmental monitoring of liquid systems such as a deep well, aquifer, lake or the like.

It is another object of the invention to provide a fiber optic probe for use in analysis of liquid systems such as a deep well or aquifer.

It is a further object of the invention to provide system and method for in situ qualitative and quantitative analysis of remote liquid systems such as a deep well or aquifer.

These and other objects of the invention will become apparent as a detailed description of representative embodiments proceeds.

SUMMARY OF THE INVENTION

In accordance with the foregoing principles and objects of the invention, a fiber optic sensor system for analyzing fluid systems is described which comprises a sampling probe which transmits tunable ultraviolet light to a sampling location, the probe including an optical fiber terminating in a sampling structure at the distal end of the probe which is inserted into the liquid to be analyzed, a light source for transmitting a selected excitation light beam to the sample location through the fiber, the resulting fluorescence characteristic of the liquid being transmitted back through the fiber structure to an optical detector. The sampling region at the end of the probe is configured to absorb or reflect away all excess excitation light so that only the resulting characteristic fluorescence is transmitted back to the detector, and may have a microporous base to exclude solid particles from the sampling region.

DESCRIPTION OF THE DRAWINGS

The invention will be more clearly understood from the following detailed description of representative embodiments thereof read in conjunction with the accompanying drawing which is a schematic in partial cutaway of a representative sensor system of the invention including detailed structure for a representative probe usable in the practice of the invention.

DETAILED DESCRIPTION

Referring now to the accompanying drawing, shown therein is a schematic of a representative sensor system 10 of the invention including representative structure for sample probe 11 according to the invention. Probe 11 may, in a preferred embodiment, comprise a generally tubular housing 13. In a unit built in demonstration of the invention, housing 13 was constructed of stainless steel tubing, 6 mm outside diameter, 5 mm inside diameter, 250 mm in length. The size and material of construction of housing 13 may otherwise comprise any suitable material and dimensions as would occur to the skilled artisan guided by these teachings, the same not considered limiting of the invention. In the sample end 15 of housing 13, a notch 16 is cut in order to define a sample region 17 for probe 11. A bundle 19 of optical fibers is disposed within housing 13 and operatively connected at a first end 20 thereof to a light source 21 and optical detector 22. Source 21 may be any suitable source for providing a light beam of selected wavelength, such as a laser source or a lamp (mercury, xenon, or others), and detector 22 may be any suitable detector type conventionally used for such purposes, such as a photomultiplier tube or a photodiode, as would occur to the skilled artisan practicing the invention, the specific selection for light source 21 and detector 22 not considered limiting of the invention. Source 21 may, in a non-limiting representative embodiment, be in the wavelength range of about 266 to 400 nm. Bundle 19 may be housed in any suitable protective conduit such as suggested in the drawing by flexible tubing segment 24 connected to housing 13. The second end 26 of bundle 19 is held within housing 13 near sample region 17 by any suitable means such as by epoxy plug 27 and an optical window 29 abutting the ends of bundle 19 substantially as suggested in the drawing. Window 29 defines the upper side of sample region 17 and may comprise suitable optical material such as glass, sapphire or quartz, as would occur to the skilled artisan guided by these teachings. Window 29 seals and protects the fiber bundle ends from direct contact with solution disposed within sample region 17 in the practice of the invention utilizing system 10. In the demonstration unit, window 29 comprised sapphire.

In accordance with a governing principle of the invention, fiber bundle 19 includes a central fiber 31 operatively connected at its first end to light source 21 for transmitting excitation light beam 32 from source 21 to sample region 17. Surrounding fiber 31 in bundle 19 is a plurality of light collection fibers 34 operatively connected at their respective first ends to optical detector 22 for collecting light emitted from sample solution within region 17 and transmitting the light emitted by the sample solution back to detector 22. It is noted that bundle 19 may comprise any suitable number of central fibers 31 and plurality of fibers 34 as would occur to the skilled artisan practicing the invention, the arrangement shown in the drawing as comprising one central fiber 31 and six fibers 34 affording an optimum compromise between sensitivity and small cross-sectional area, and which was the structure made and used in demonstration of the invention. It is noted further that, in certain applications for the invention, such as in the measurement of highly turbid samples or in measurements requiring minimization of sensor cross-sectional area, fiber bundle 19 may be replaced by a single fiber operatively connected at the first end thereof to light source 21 and to detector 22.

The base 36 of probe 11 includes a plate 37 of glass, mirrored surface, ultraviolet-absorbing filter, or any other suitable material occurring to the skilled artisan practicing the invention, for defining the lower extremity of sample region 17. The material selected for plate 37 is made to be substantially absorbing of ultraviolet light comprising beam 32, and plate 37 is disposed at an angle as suggested in the drawing sufficient to divert the reflected component of beam 32 away from sample region 17 so as to prevent any portion of beam 32 from being reflected back into fibers 34 in the practice of the invention as described more fully below. In the unit built in demonstration of the invention, plate 32 comprised a glass microscope slide segment disposed at an angle a of about 25° to a normal to beam 32 (for desirable plate 37 materials angle a generally is in the range of from about 20° to 30°).

In the practice of the invention, sample end 15 may be inserted into a solution to be analyzed so that the solution flows into and fills sample region 17. Excitation light of selected wavelength is transmitted from source 21 along central fiber 31 into sample region 17 as light beam 32. As suggested above, beam 32 passes through sample region 17 onto plate 37 which may absorb a substantial portion of beam 32 and reflect away from sample region 17 any remaining light incident thereon. For most solutions analyzed in the practice of the invention, light in the short wavelength ultraviolet (UV) end of the spectrum was used in the range of from about 266 to 295 nm. It is noted, however, that within the scope of these teachings and of the appended claims, light of substantially any optical wavelengths utilizing any suitable source selected by one skilled in the art guided by these teachings may, for the analysis of selected fluid systems, be used for analysis, depending on the constituent to be tested for in the fluid system being analyzed. In Table I are presented typical sample solution constituents, and the corresponding excitation wavelengths and resulting fluorescence wavelengths which may be obtained in the use of the invention. Fluorescence and scattered light characteristic of the solution within sample region 17 resulting from optical excitation of molecules in the solution is emitted substantially isotropically from sample region 17, and a portion of the emitted light enters collection fibers 34 and is transmitted to detector 22. In the single fiber configuration suggested above, excitation light may be transmitted down the single fiber and to sample region 17 and any resulting fluorescence from the solution may be transmitted back along the same fiber to the detector 22. In order to correct the signals detected from sample region 17 for turbidity conditions within the solution being analyzed, a layer of fluorescent filter 39 may be disposed beneath plate 37 as suggested in the drawing. The turbidity corrections are made at a wavelength which is not absorbed by the solution within sample region 17 or by plate 37 (i.e., longer wavelength light). The amount of fluorescence which is returned by filter 39 to detector 22 can be calibrated as a function of turbidity, yielding a correction to the fluorescence signal obtained from the solution for the selected incident excitation wavelength.

TABLE I

| Sample Constituent | Excitation Wavelength (nm) | Characteristic Fluorescence Wavelength (nm) |
|---|---|---|
| Benzene | 253 | 284 |
| Toluene | 261 | 284 |
| p-Xylene | 274 | 291 |
| Naphthalene | 285 | 335 |
| Anthracene | 270 | 420 |

The system of the invention may be used for the in situ measurement of environmental contaminants of deep well water, aquifer water and the like, or for the analysis of other remote solutions. Expensive and time-consuming sample collection, transport, preparation, and laboratory analysis may therefore be substantially avoided. The system is rugged in construction and simple and inexpensive in operation and may be adapted to battery power for portability of the system. Because the system may be constructed to provide a fixed path length for the excitation light, quantitative concentration measurements may be made.

The invention therefore provides a fiber optic sensor system for on-site monitoring of environmental contaminants. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A fiber optic sensor system for use in the analysis of fluid systems, comprising:
   (a) a light source;
   (b) an optical detector;
   (c) a sampling probe having first and second ends, and including a sampling region at said second end thereof for immersion into a fluid system to be analyzed;
   (d) said sampling probe including an optical fiber operatively connected at a first end thereof to said light source and said optical detector, said fiber terminating at said second end thereof near a first end of said sampling region, whereby light from said light source is transmitted along said fiber into said sampling region and light from a sample within said sampling region is transmitted along said fiber to said optical detector; and (e) the second end of said sampling region including means for absorbing or reflecting light from said light source away from said sampling region whereby only light from said sample within said sampling region is transmitted from said sampling region back along said fiber to said detector.

2. The system of claim 1 wherein said probe includes a generally tubular housing for containing said fiber, said tubular housing having a notch defined near the second end thereof defining said sampling region.

3. The system of claim 1 further comprising an optical window abutting said second end of said fiber and defining said first end of said sampling region.

4. The system of claim 3 wherein said optical window comprises an optical material selected from the group consisting of glass, sapphire and quartz.

5. The system of claim 1 wherein said light source is in the wavelength range of about 266 to 400 nm.

6. The system of claim 5 wherein said light source is a laser, a mercury lamp or a xenon lamp.

7. The system of claim 1 wherein said detector is a photomultiplier tube or a photodiode.

8. The system of claim 1 wherein said second end of said sampling region includes a reflective surface disposed at an angle of from about 20° to 30° to a normal to the propagation direction of said light from said light source.

9. The system of claim 1 further comprising a fluorescent filter at said second end of said sampling region.

10. A fiber optic sensor system for use in the analysis of fluid systems, comprising:

(a) a light source;

(b) an optical detector;

(c) a sampling probe having first and second ends, and including a sampling region at said second end thereof for immersion into a fluid system to be analyzed;

(d) said sampling probe including an optical fiber bundle comprising a plurality of optical fibers each having respective first and second ends, at least one of said fibers being operatively connected at a first end thereof to said light source and the remaining said fibers operatively connected to said optical detector, each of said plurality of said fibers terminating at the respective second ends thereof near a first end of said sampling region, whereby light from said light source, is transmitted along said at least one of said fibers into said sampling region and light from a sample within said sampling region is transmitted along said remaining said fibers to said optical detector; and (e) the second end of said sampling region including means for absorbing or reflecting light from said light source away from said sampling region whereby only light from said sample within said sampling region is transmitted from said sampling region back along said remaining said fibers to said detector.

11. The system of claim 10 wherein said optical fiber bundle includes a central first fiber operatively connected at the first end thereof to said light source for transmitting light from said light source to said sampling region, said central first fiber surrounded by a plurality of second fibers operatively connected at the respective first ends thereof to said optical detector for transmitting light from said sampling region to said optical detector.

12. The system of claim 10 further comprising an optical window abutting respective said second ends of said plurality of optical fibers and defining said first end of said sampling region.

13. The system of claim 12 wherein said optical window comprises an optical material elected from the group consisting of glass, sapphire and quartz.

14. The system of claim 10 wherein said light source is in the wavelength range of about 266 to 400 nm.

15. The system of claim 14 wherein said light source is a laser, a mercury lamp or a xenon lamp.

16. The system of claim 10 wherein said detector is a photomultiplier tube or a photodiode.

17. The system of claim 10 wherein said second end of said sampling region includes a reflective surface disposed at an angle of from about 20° to 30° to a normal to the propagation direction of said light from said light source.

18. The system of claim 10 wherein said probe includes a generally tubular housing for containing said optical fiber bundle, said tubular housing having a notch defined near the second end thereof defining said sampling region.

19. The system of claim 10 further comprising a fluorescent filter at said second end of said sampling region.

* * * * *